United States Patent [19]
Holt et al.

[11] Patent Number: 6,017,766
[45] Date of Patent: Jan. 25, 2000

[54] PROCESS FOR MEASURING CONCENTRATION OF NONIONIC SURFACTANTS IN AN AQUEOUS ALKALINE SOLUTION

[75] Inventors: Rodica Holt, Far Hills; Joseph E. Oberlander, Phillipsburg; Eleazar B. Gonzalez, Bloomfield; Pilarcita L. Ranque, Flemington; Maria F. Y. Calindas, New Brunswick, all of N.J.

[73] Assignee: Clariant Finance (BVI) Limited, Virgin Islands (Br.)

[21] Appl. No.: 09/014,387

[22] Filed: Jan. 28, 1998

[51] Int. Cl.$^7$ ..................................... G01N 21/78
[52] U.S. Cl. ........................ 436/164; 436/166; 436/178
[58] Field of Search .................................... 436/164, 166, 436/178

[56] References Cited

U.S. PATENT DOCUMENTS

| | | | |
|---|---|---|---|
| 4,602,963 | 7/1986 | Piatkowski | 436/166 |
| 4,732,836 | 3/1988 | Potvin et al. | 430/192 |
| 4,863,827 | 9/1989 | Jain et al. | 430/145 |
| 5,039,595 | 8/1991 | Schwam et al. | 430/326 |

OTHER PUBLICATIONS

BASF Corporation, Performance Review, 1991.

Analytical Biochemistry 187, 54–55 (1990) "Colorimetric Assay for Pluronic F–68 as Measured in Isolated Rat Liver Perfusion Systems" A. M. Tercyak et al.

Environmental Science & Technology, vol. 11, p. 1167, Dec. 1977, American Chemical Society, "Analytical Method for Nonionic Surfactans in Laboratory Biodegradation and Environmental Studies" Boyer et al.

5540 B. Surfactant Separation by Sublation pp. 5–34–5–36, and 5540 D. Nonionic Surfactants as CTAS pp. 5–39–5–41.

*Primary Examiner*—Jeffrey Snay

[57] ABSTRACT

The present invention is a process for precisely measuring the concentration of a nonionic surfactant in an aqueous alkaline solution. The process comprises extracting the surfactant into an organic solvent, separating the solvent and forming a colored complex that can be quantitatively measured to give the actual concentration of the surfactant.

8 Claims, No Drawings

PROCESS FOR MEASURING CONCENTRATION OF NONIONIC SURFACTANTS IN AN AQUEOUS ALKALINE SOLUTION

BACKGROUND

This invention relates to an efficient and precise method for determining the concentration of a nonionic surfactant in an aqueous alkaline solution. Aqueous alkaline solutions, such as developers, are used extensively in photolithography as a chemical component of the imaging process, particularly in the manufacture of integrated circuits. Developers interact with the photoresists to delineate an image on the substrate. These developers comprise an aqueous solution of a base and sometimes a surfactant. Surfactants, in developers, are often desirable, especially nonionic surfactants since they impart a degree of wettability between the aqueous phase and the photoresist coating and, furthermore, can improve the lithographic properties of the photoresist. The chemical composition and concentration of the surfactant is critical to the efficacy of the developer, and the quality and reproducibility of the developed image. Thus, it is important to have an analytical method that can accurately determine the concentration of a nonionic surfactant in a developer.

Photoresists are well known to those skilled in the art. Generally speaking, they must be sensitive to light so that patterns can be formed in them and they must selectively resist subsequent etching or other processing so that the pattern can be transferred to the underlying substrate. The dominant photoresist system employed in integrated circuit manufacturing today is the novolak/diazonaphthoquinone combination. Diazonaphthoquinones of the class employed in positive photoresists are typically formed by the reaction of a naphthoquinone diazide sulfonyl chloride with a phenolic compound. Reaction products thus formed might include the naphthoquinone (1,2) diazide (5)-sulfonyl, naphthoquinone (1,2) diazide (4)-sulfonyl, naphthoquinone (2,1) diazide (5)-sulfonyl, or naphthoquinone (2,1) diazide 4-sulfonyl radicals or mixtures thereof. Of course, the sulfonate esters thus synthesized might include the residue of any suitable phenolic compound. These diazides are fairly nonpolar organic molecules that are soluble in organic solvents, but not very soluble in water. Upon exposure to light, diazonaphthoquinone photoactive compounds form a polar, base-soluble carboxylic acid in accordance with mechanisms known to skilled artisans. Thus, using an aqueous base as the developer, the exposed photoactive compound is relatively soluble, while the unexposed photoactive compound is relatively insoluble; creating a solubility difference which is the basis of image formation.

It is not sufficient, however, to simply change the solubility of the photoactive compound, rather, the entire photoresist mixture must change its solubility. Thus, the interaction of the photoactive (photosensitive) compound with the binder resin is likewise an important consideration, as is its absorption spectrum. Accordingly, positive photoresist compositions generally include a phenol-formaldehyde resin of the novolak class or sometimes a hydroxystyrene polymer such as poly(4-hydroxystyrene). Other polymeric components, including styrene, methyl styrene, styrene-maleic anhydride components in combination with the foregoing may also be employed. See, generally, U.S. Pat. Nos. 4,732,836 and 4,863,827 for further information relating to positive photoresists, and incorporated herein by reference.

Of considerable importance in the imaging of photoresists is the selection of a developer composition and developer process, since development is a key aspect of the integrated circuit production process. Developers containing different types of surfactants are known in the art and surfactants are used to impart certain desirable properties to the development process, such as wettability, cleanliness of the substrate after the imaging process, improvement of the lithographic properties of the photoresist, etc. One particular type of surfactant that is used in developers is nonionic, especially the block copolymers of ethylene oxide and propylene oxide. Other nonionic surfactants, such as ethoxylated alcohols, ethoxylated alkyl phenols and fluorinated polymers may also be used. In U.S. Pat. No. 5,039,595 to Schwalm et al, and incorporated herein by reference, there is described another aqueous developer with a heterocyclic hydroxyalkyl compound as the base. It is noted in the '595 patent that the following surfactants may be used: nonylphenoxypoly(ethyleneoxy)-ethanol, octylphenoxypoly (ethyleneoxy)-ethanol or commercial fluorinated surfactants (col. 4, lines 45–51).

Not only does the chemical composition effect the development process of the photoresist, so does the concentration of the surfactant. Thus it is critical to be able to monitor the concentration of the nonionic surfactant and to manufacture it consistently within the customer's specifications. This patent relates to a novel method of precisely isolating and quantifying the nonionic surfactant in the aqueous alkaline developer.

Methods are known for the isolation and spectrophotometric analysis of nonionic polymers, especially those that rely on the ability of a cobalt compound to complex with polyether linkages. When a solution of cobalt nitrate and ammonium thiocyanate, herein called a cobalt thiocyanate solution, is added to the surfactant, a colored dye is formed which can be monitored spectrophotometrically. These methods were found by the inventors not to work when the nonionic polyether surfactant is present in an alkaline solution, as is the case with developers used in photolithography. The prior art, specifically, BASF Procedure (100, Cherry Hill Road, Parsippany, N.J. 07054), "Standard methods for examination of water and wastewater" (Section 5540B&D, American Public Health Association, 1015 Fifteenth St. NW, Washington D.C. 20005) and "Analytical method for nonionic surfactants in laboratory biodegradation and environmental studies" (Environmental Science and Technology, Vol.11, 1167, 1997), recommends isolating the surfactant from the solution in the solid form by sublation, then redissolving it in an organic solvent and forming a cobalt complex which can further be assayed spectrophotometrically. This method is cumbersome, involving many steps consisting of nitrogen bubbling, collection of the surfactant in ethyl lactate, evaporating the surfactant to dryness and dissolving the surfactant in methylene chloride. Each step can potentially increase the error of measurement. Furthermore, large quantities of the developer must be used to yield an amount of solid surfactant that can reliably be quantified, especially where only small amounts of surfactant are present in the developer. Thus, a process requiring the simplification and minimization of steps is highly desirable from a manufacturing quality control perspective. The reference, "Colorimetric assay for Pluronic F-68 as measured in isolated rat liver perfusion systems" (Analytical Chemistry Vol. 187, 54, 1990), discloses an analytical method where the aqueous solution of the Pluronic F68 surfactant is dried to give the surfactant, dissolved in water, the cobalt complex of the surfactant is formed, ethyl lactate is added and the precipitated dye dissolved in acetone and the dye is assayed spectrophotometrically to give the concentration of the surfactant. Again, this is a technique with many steps, particularly the undesirable isolation step of the solid surfactant, and with an increased propensity of errors. Furthermore, this technique recommends the addition of cobalt thiocyanate to an aqueous solution, which was found to be unsuitable for alkaline solutions.

Due to the long and tedious procedures proposed by the prior art, a new simple process was developed and this patent discloses an efficient and reproducible method of extracting and quantifying a nonionic polymer from an aqueous alkaline solution.

SUMMARY

The object of the present invention is to provide a process for measuring the concentration level of a nonionic surfactant in an aqueous alkaline solution, where the process gives an accurate quantitative measurement and where the process comprises the minimum complexity such that it can lead to good precision and be cost-effective.

The present invention is a novel process for measuring the amount of non-ionic surfactant in an aqueous alkaline solution, comprising:
a) adding an organic solvent to the aqueous alkaline solution and extracting the nonionic surfactant from the aqueous alkaline solution into the organic solvent;
b) separating the organic phase which contains the nonionic surfactant;
c) adding a solution of a complexing agent to the organic phase and holding it for a sufficient time to fully react the complexing agent with the nonionic surfactant to form a colored dye;
d) measuring an absorption of the colored dye and thereby measuring the amount nonionic surfactant in the aqueous alkaline solution.

The invention preferably uses methylene chloride as the organic solvent and cobalt thiocyanate as the complexing agent. The holding time for the cobalt thiocyanate and surfactant adduct if preferably greater than 30 minutes.

DESCRIPTION

The present invention relates to a process for measuring the concentration of a nonionic surfactant in an aqueous alkaline solution, especially developers. Developers used in the lithography typically comprise an aqueous solution of a base, such as tetralkyl ammonium hydroxide, sodium hydroxide, potassium hydroxide and the like. Many types of surfactants are added to the developer since surfactants impart useful properties to the developer, such as wettability, cleanliness of the substrate after development and improvement of lithographic properties of photoresists. Nonionic surfactants have been found to be particularly useful since they are known to be low-foaming, have good cold water solubility and have low critical micelle concentration. Especially useful are copolymers of ethylene oxide and propylene oxide, fluorinated, ethoxylated and siloxane surfactants. It has also been found that the concentration of the surfactant must be kept within a specific range in order for the desired properties of the developer to be maintained, and it was for this reason that a novel process was developed to accurately measure the concentration of the surfactant in an alkaline solution.

It was found through experimentation that if the cobalt thiocyanate solution is added directly to the surfactant containing developer, then, due to the very basic conditions of the developer, a precipitate forms which cannot be quantitatively assayed. Isolating the surfactant in the solid form from the developer by bubbling or evaporation was not considered feasible due to the difficulties inherent to these methods, especially for low levels of surfactant. The novel process of this invention is a simpler process, comprising, adding an organic solvent, extracting the surfactant into the organic phase, removing the aqueous phase, adding the cobalt thiocyanate solution directly to the organic phase and measuring the absorption of the dye formed and thereby calculating the concentration of the surfactant. The surfactant forms a complex with cobalt compound to give a brightly colored dye which can be quantitatively assayed to give the actual concentration of the surfactant. Typically, standards containing known concentrations of the same surfactant in the aqueous alkaline solution are run together with the sample whose concentration needs to be measured and a calibration curve determines the exact concentration of the surfactant in the unknown sample. It is within the scope of this invention that complexing agents other than cobalt thiocyanate may be used, provided they can form a colored complex with the nonoionic surfactant. Other cobalt salts may be used or salts of other transition metals.

Calibration samples are prepared by adding known amounts of the surfactant to the aqueous alkaline developer made from deionized water and a base. The base may be sodium or potassium hydroxide, but is preferably tetramethyl ammonium hydroxide or chorine. The concentration of the base in the developer is typically between 1 weight percent to 5 weight percent, preferably 2–3 weight percent. The calibration samples preferably contain the amount of surfactant that is in the range of the unknown sample. For example if the unknown has an estimated surfactant concentration of 200 ppm, then the standards may range from 0 to 2500 ppm of surfactant.

In most cases a salt, like sodium chloride or potassium chloride, is added to the samples prior to the addition of the organic solvent. The salt is known to reduce the foaming capacity of the surfactant and make the isolation of the surfactant easier, and any salt that is known to do this may be used. Once the salt has dissolved, the organic solvent is added to the solutions in order to extract the surfactant. Small repeated extractions, preferably three times, was found to give good results, although the number of extractions is determined by the surfactant type and quantity of solvent used. Solvents that may be used are those that are effective in extracting the surfactant from the aqueous phase and which do not mix with the aqueous phase. One particular solvent that was found to be effective was methylene chloride, although others may also be used, like xylene, toluene and butylacetate.

Once the extraction of the surfactant into the organic phase is complete, the aqueous phase is removed and the extractants combined. To the extractant is then added an aqueous cobalt thiocyanate solution. The removal of the basic aqueous solution prior to the addition of the cobalt thiocyanate prevents any interference when forming the cobalt-surfactant dye. It was unexpectedly found that the time between adding the cobalt thiocyanate solution and the measurement of the absorbency of the dye is critical to the accuracy of the test. The data showed that a minimum of 30 minutes, preferably 1–2 hours, holding time is required, before a stable absorptivity reading is achieved.

An ultraviolet spectrophotometer is used to measure the absorbency of the dye complex, preferably at the peak maximum. The cobalt complex gives absorption peaks at around 318 nm or around 620 nm. A calibration curve is obtained from the plot of concentration against absorbency of the standard samples. This plot can then be used to give the exact concentration of the sample with the unknown surfactant concentration.

The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLE 1

(Comparative)

A solution consisting of 5 ml of 1000 ppm Noigen EP120A surfantant in deionized (DI) water (available from Dai-lchi Kogyo Seiyaku Co., Ltd., 7F. Shin Kyoto Center Building, Karasuma Nishiiru, Shiokojidori, Shimogyo-ku, Kyoto, KYO 600, Japan) and 50 ml AZ® 300MIF developer (an aqueous tetramethyl ammonium hydroxide solution, available from Clariant Corp., AZ® Electronic Materials, 70 Meister Ave., Somerville, N.J. 08876) and 50 ml DI water was prepared in a 250 ml separatory funnel.

20 g of sodium chloride was dissolved in the 250 ml separatory funnel. To this funnel was added 10 ml of cobalt thiocyanate solution, prepared by combining 208 g of ammonium thiocyanate and 93 g of cobalt nitrate hexahydrate in 100 ml water. A precipitate formed immediately which made further analysis inaccurate and thus the method failed.

EXAMPLE 2

A stock solution consisting of 100 mg Tetronic® 701 surfactant (available from BASF Co., 100, Cherry Hill Road, Parsippany, N.J. 07054.) and 100 ml deionized (DI) water was prepared. Three calibration samples were made using 0.5, 2.5 and 5 ml of the stock solution and diluted with 50 ml AZ® 300MIF developer (an aqueous tetramethyl ammonium hydroxide solution, available from Clariant Corp., AZ® Electronic Materials, 70 Meister Ave., Somerville, N.J. 08876) and 50 ml DI water were added to a 250 ml separatory funnel.

Into each of the separatory funnels was dissolved 20 g of sodium chloride. The surfactant was extracted from each solution by adding 10 ml methylene chloride to the funnel, shaken and then the methylene chloride was separated and put into a 25 ml flask. This was repeated with another 10 ml and then another 5 ml of methylene chloride. All the methylene chloride was collected into the 25 ml flask and topped off with methylene chloride to the 25 ml mark. This extraction procedure was repeated with all the samples. 1 ml of cobalt thiocyanate solution, prepared by combining 208 g of ammonium thiocyanate and 93 g of cobalt nitrate hexahydrate in 100 ml water, was added to each flask. The solutions were left for 30 minutes and the solutions became colored. The top aqueous layer was removed and the solutions left for 2 hours. The absorption of all the samples was measured at 620 nm using an ultraviolet spectrometer. The absorption of the standard samples was plotted and a calculated. Typically, a correlation coefficient of greater than 0.8 shows a good relationship between concentration and absorption and can be used to determine the unknown concentration of a surfactant sample.

This procedure was repeated with other nonionic surfactants and the results of the different surfactants are given in Table 1. The data, which shows good correlation coefficients, illustrates that the novel testing process of this invention can be used to accurately analyze the surfactant concentration in an aqueous alkaline solution.

TABLE 1

Evaluation of surfactants tested

| Trade Name | Chemical Family | Surfactant Type | Correlation co-efficient (R squared) |
|---|---|---|---|
| Emery 6706 | Polyethoxylated phenol | Non-ionic | 0.9942 |
| Fluorad FC-170C | Fluorinated Alkyl Polyoxyethylene | Non-ionic | 0.9406 |
| Hodag 8025R | Polyether modified siloxane | Non-ionic | 0.9934 |
| Macol ® 16 | Block EO/PO | Non-ionic | 0.8539 |
| Noigen EP120A | Polyethoxylated phenol | Non-ionic | 0.9808 |
| Pluronic ® F68 | Block EO/PO | non-ionic | 0.9723 |
| Pluronic ® L92 | Block EO/PO | non-ionic | 0.9817 |
| Pluronic ® 10R5 | Block EO/PO | non-ionic | 0.9998 |
| Pluronic ® 31R1 | Block EO/PO | non-ionic | 0.9885 |
| Pluronic ® 25R2 | Block EO/PO | non-ionic | 0.9964 |
| Surfynol ® 440 | Ethoxylated tetra-methyl decyndiol | Non-ionic | 0.9899 |
| Tetronic ® 701 | Block EO/PO | non-ionic | 0.9980 |

Pluronic® and Tetronic® are trademarks of BASF Corp. 100, Cherry Hill Road, Parsippany, N.J. 07054.

Macol® is a trademark of PPG Industries, 3938, Porett Dr., Gurnee, Ill. 60031.

Fluorad FC-170C was purchased from 3M Company, 3M Center Building 223, St. Paul, Minn. 55144.

Surfynol® is a trademark of Air Products and Chemical Co., 7201 Hamilton Boulevard, Allentown, Pa. 18195.

Hodag was purchased from Calgene Chemical Co., 7247 North Central Park Avenue, Skokie, Ill. 60076.

Emery 6706 was purchased from Henkel Corp., 5051 Estecreek Drive, Cincinnati, Ohio 45232.

Noigen EP-120A was purchased from Dai-Ichi Kogyo Seiyaku Co., Ltd., 7F. Shin Kyoto Center Building, Karasuma Nishiiru, Shiokojidori, Shimogyo-ku, Kyoto, KYO 600, Japan.

Example 3

An experiment was run to determine the unknown concentration of Tetronic® 701 surfactant in AZ® 300MIF developer. To 50 ml of AZ® 300MIF developer was added about 3.75 ml of a solution of 1000 ppm Tetronic® 701 surfactant in DI water. The experiment was run as in Example 2, using the calibration samples and with the additional unknown sample. The results are given in the Table2 below.

TABLE 2

| Sample | Concentration, (ug) | Absorbency @ 620 nm | Comments |
|---|---|---|---|
| STD0 | 0 | 0.012 | Correlation Coefficient = 0.9916 |
| STD1 | 620 | 0.042 | |
| STD2 | 3100 | 0.187 | |
| STD3 | 6200 | 0.437 | |
| UNKNOWN | | 0.278 | Calculated Value = 81 ppm of surfactant |

We claim:

1. A process for measuring the amount of non-ionic surfactant in an aqueous alkaline solution, comprising:

a) adding a salt to the aqueous alkaline solution;

b) adding an organic solvent to the aqueous alkaline solution and extracting the nonionic surfactant from the aqueous alkaline solution into the organic solvent;

c) separating the organic phase which contains the non-ionic surfactant;

d) adding a solution of a complexing agent to the organic phase and holding it for at least 30 minutes to form a colored dye;

e) measuring an absorption of the colored dye and thereby measuring the amount nonionic surfactant in the aqueous alkaline solution.

2. The process of claim 1, where the complexing agent is a solution of cobalt thiocyanate.

3. The process of claim 2, where the cobalt thiocyanate is formed by mixing ammonium thiocyanate and cobalt nitrate hexahydrate in water.

4. The process of claim 1, where the salt is selected from sodium chloride and potassium chloride.

5. The process of claim 1, where the aqueous alkaline solution comprises the nonionic surfactant, water and an alkali selected from tetraaklylammonium hydroxide, choline, sodium hydroxide and potassium hydroxide.

6. The process of claim 1, where the organic solvent is selected from methylene chloride, toluene and xylene.

7. The process of claim 1, where the surfactant is a polyether surfactant.

8. The process of claim 1, where the surfactant is a copolymer of ethylene oxide and propylene oxide, ethoxylated surfactant, fluorinated/polyoxyethylene surfactant, polyether siloxane surfactant.

* * * * *